(12) United States Patent
Heiner et al.

(10) Patent No.: US 6,585,728 B2
(45) Date of Patent: Jul. 1, 2003

(54) CRYOABLATION CATHETER WITH AN IMPROVED GAS EXPANSION CHAMBER

(75) Inventors: Peter Wilfred Heiner, Bakkeveen (NL); Bart-Jan Korteling, Mission Viejo, CA (US)

(73) Assignee: Biosense Webster, Inc., Diamond Bar, CA (US)

(*) Notice: Subject to any disclaimer, the term of this patent is extended or adjusted under 35 U.S.C. 154(b) by 0 days.

(21) Appl. No.: 09/865,641

(22) Filed: May 25, 2001

(65) Prior Publication Data

US 2002/0177845 A1 Nov. 28, 2002

(51) Int. Cl.⁷ .............................................. A61B 18/02
(52) U.S. Cl. ........................... 606/21; 606/20; 606/32
(58) Field of Search ..................................... 606/20–23

(56) References Cited

U.S. PATENT DOCUMENTS

| | | | |
|---|---|---|---|
| 3,910,277 A | 10/1975 | Zimmer | |
| 3,924,628 A * | 12/1975 | Droegemueller et al. | 606/21 |
| 4,646,735 A * | 3/1987 | Seney | 128/DIG. 27 |
| 5,139,496 A | 8/1992 | Hed | |
| 5,281,213 A | 1/1994 | Milder et al. | |
| 5,281,215 A | 1/1994 | Milder | |
| 5,423,807 A | 6/1995 | Milder | |
| 5,520,682 A * | 5/1996 | Baust et al. | 606/20 |
| 5,993,444 A * | 11/1999 | Ammar et al. | 606/21 |
| 6,241,722 B1 * | 6/2001 | Dobak et al. | 606/20 |
| 6,270,493 B1 * | 8/2001 | Lalonde et al. | 606/23 |

\* cited by examiner

*Primary Examiner*—Linda C. M. Dvorak
*Assistant Examiner*—Henry M. Johnson, III

(57) ABSTRACT

A cryoablation catheter having a high efficiency gas expansion chamber comprised of a generally cylindrical or hemispherical cooling chamber having a wall thickness equal to approximately one half the wall thickness of the walls of the catheter in order to provide a cooling chamber increased with large gas expansion volume and having thin walls for rapid cooling of the outside surface of the cooling chamber.

10 Claims, 2 Drawing Sheets

CRYOABLATION CATHETER WITH AN IMPROVED GAS EXPANSION CHAMBER

BACKGROUND OF THE INVENTION

1. Field of the Invention

The present invention relates to a cryoablation catheter, and more particularly to a cryoablation catheter for ablating heart tissue.

2. Description of the Prior Art

Certain medical procedures are performed using minimally invasive surgical techniques wherein one or more slender implements are inserted through one or more small incisions into a patient's body. In the case of an ablation procedure, the surgical implement may include a rigid or flexible structure, or catheter, having an ablation device at or near its distal end that is placed adjacent to the tissue to be ablated. Radio frequency energy, microwave energy, laser energy, extreme heat, or extreme cold may be provided by the ablation device to destroy the tissue.

In certain cardiac procedures, such as the treatment of cardiac arrhythmias, selective ablation of cardiac tissue may be used to eliminate the source of the arrhythmia. One minimally invasive procedure, i.e., radio frequency (RF) catheter ablation, includes a preliminary step of conventional electrophysiology mapping followed by the creation of one or more ablated regions (lesions) in cardiac tissue using RF energy. Multiple lesions are frequently required because the effectiveness of each of the lesion sites cannot be predetermined with exactness due to limitations of conventional mapping. Often, five lesions, and sometimes as many as twenty lesions may be required before a successful result is attained.

Some deficiencies of radio-frequency ablation devices and techniques have been overcome by ice mapping prior to creating lesions, as taught by U.S. Pat. Nos. 5,423,807; 5,281,213 and 5,281,215. However, even though combined cryogenic mapping and ablation devices permit greater certainty and less tissue damage than RF devices and techniques, both the cryogenic and the RF devices are configured for spot or roughly circular tissue ablation.

Spot tissue ablation is acceptable for certain procedures. However, other procedures can be more therapeutically effective if multiple spot lesions are made along a predetermined line, or linear lesion, is created in a single ablative step. Radio-frequency ablation devices are known to be able to create linear lesions by dragging the ablation tip along a line while the ablation electrode is energized.

One problem associated with presently existing cryoablation catheters is that the outside dimensions of the cooling chamber, which is disposed at the distal tip of the catheter, must be limited by the size of the vessel. In other words, the outside diameter of the cooling chamber must be slightly smaller than the inside diameter of the vessel in order to permit passage of the cooling chamber through the vessel. Such small cooling chambers are relatively inefficient. It would be far better to have a cryoablation catheter with a large cooling, or gas expansion chamber, in order to increase the cooling efficiency of the device.

In the past it has been thought to be desirable to have a thick-walled cooling chamber, or dome, positioned at the distal tip of a catheter to serve both as an expansion chamber and a "heat sink" to remove heat in order to cool adjacent tissue. Such thick-walled chambers present two problems with respect to efficient cooling and ablation. One problem is that with a thick-walled chamber having an outside diameter small enough to pass through the vasculature of the human body, the volume of the internal expansion chamber is very small. With a small volume cooling chamber, the cooling efficiency is very poor. In addition, the time required to cool such a thick-walled device is much greater than is required for a very thin-walled device. In other words, such prior devices have incorporated thick-walled cooling chambers in order to take advantage of the "heat sink" effect, but with a significant loss in cooling efficiency.

SUMMARY OF THE INVENTION

The present invention provides a cryogenic ablation system with significantly improved cooling efficiency and reduction in cooling time.

In accordance with one aspect of the present invention there is provided a cryoablation catheter which includes an elongated flexible outer tubular member having a lumen extending therethrough, an inner tubular member extending through the lumen of the elongated flexible outer tubular member, and a generally cylindrical fluid expansion cooling chamber disposed on the distal end of the outer tubular member. The cooling chamber is in fluid engagement with the lumen of the outer tubular member. The cooling chamber also has an inside diameter substantially greater than the inside diameter of the outer tubular member and an outside diameter substantially equal to the outside diameter of the outer tubular member. The inner tubular member includes a proximal end adapted to be coupled to a source of cryoablation fluid, and also includes a fluid expansion nozzle disposed on its distal end which extends into the cooling chamber. Cooling fluid is applied to the proximal end of the inner tubular member and the fluid is caused to expand at the nozzle to thereby cause cooling to occur within the cooling chamber.

In accordance with another aspect of the present invention, the fluid expansion cooling chamber generally takes the form of a hemisphere, or dome, having an inside diameter substantially greater than the inside diameter of the outer tubular member and an outside diameter substantially equal to the outside diameter of the outer tubular member.

In accordance with still another aspect of the present invention, the outer wall of the cooling chamber is significantly thinner than the thickness of the outer tubular member, and is preferably approximately one-half of the thickness of the outer tubular member. More particularly, the cooling chamber preferably includes side walls having a thickness of about 0.10 inches. In another embodiment of the present invention, the fluid expansion nozzle takes the form of a Jewel-Thompson fluid expansion nozzle. The gas used for expansion and cooling preferably takes the form of nitrous oxide.

In accordance with still another embodiment of the present invention, the cryoablation catheter includes one or more mapping electrodes mounted on the distal end of the outer tubular member in order to provide a mapping function used in conjunction with the ablation procedure.

These and other objects of the present invention will be understood from the description of a preferred embodiment of the invention which follows.

BRIEF DESCRIPTION OF THE DRAWINGS

Further properties, advantages and measures according to the present invention will be explained in greater detail in the description of a preferred embodiment, with reference to the attached figures in which.

DESCRIPTION OF THE PREFERRED EMBODIMENT

Figure 1:
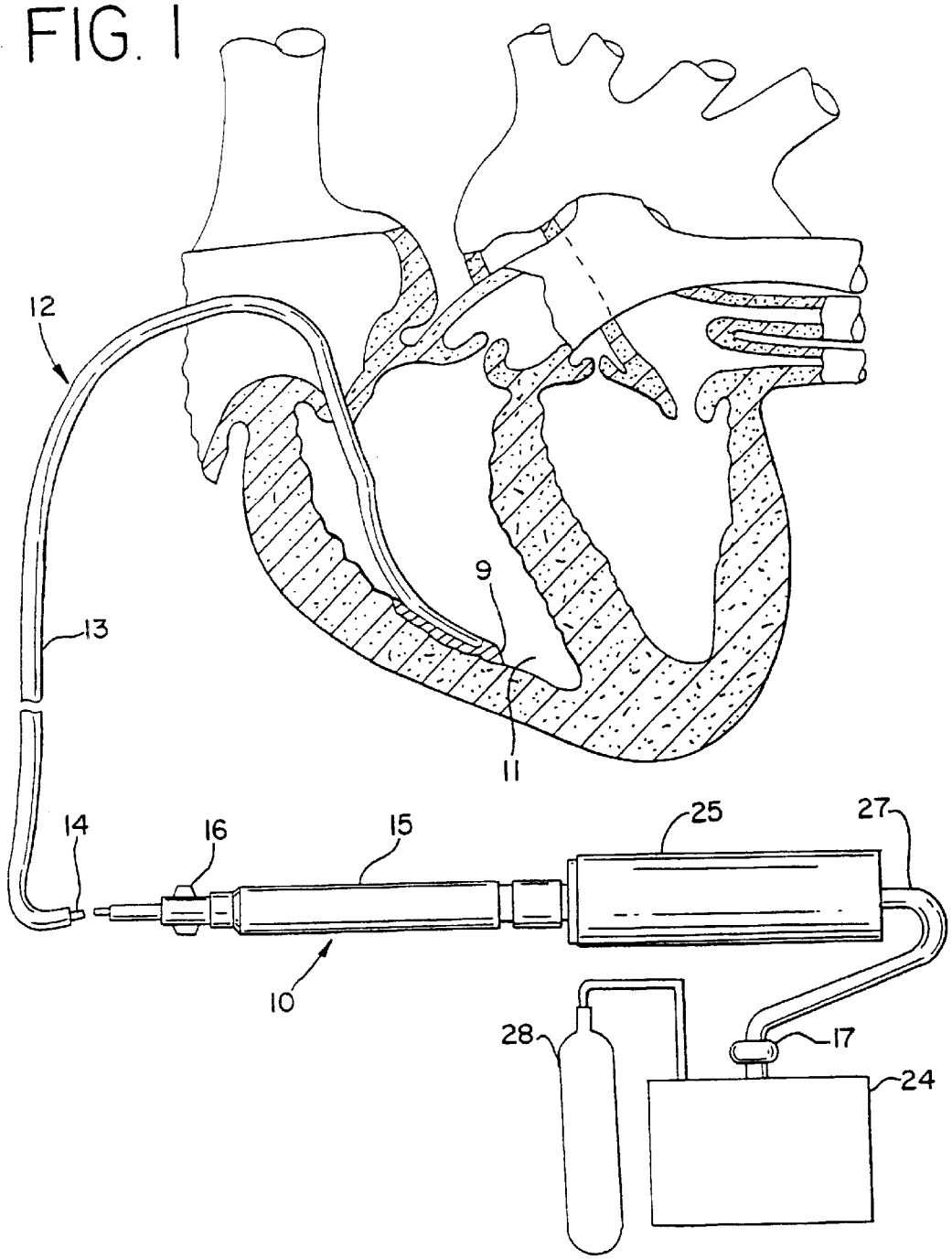
FIG. 1 is a schematic view of a cryoablation system including a cryoablation catheter according to the present invention shown with respect to a human heart; and, FIG. 2 illustrates in detail the distal portions of a cryoablation catheter including an improved cooling chamber in accordance with the present invention.

FIG. 1 illustrates one embodiment of a cryoablation catheter system 10 according to the present invention which includes a catheter 12. The catheter 12 comprises an outer body 13, an inner body 14, a handle 15 and a control knob 16. The control knob 16 is movable in the axial direction in relation to the handle 15 in such a way that the distal tip of the catheter 12 is deflectable.

The handle 15 is connected to a heat exchanger 25, which is in turn coupled through a connecting tube 27 to a control unit 24. A control valve 17 is disposed in the connecting tube 27 and serves to control the flow of gas from a gas cylinder 28, preferably containing $N_2O$. By way of an alternative, gases other than $N_2O$ may be used for this purpose.

The control valve 17 constitutes the control means with which the flow of $N_2O$ through the inner body 14 is regulated. The pressure depends on the intended effect of the cryoablation at the distal tip of the catheter 12.

The tip at the distal end of the catheter 12 may also be provided with other measurement equipment to determine the position of the nozzle 50 for instance. Examples of such measuring equipment are marking rings which are recognizable when using imaging techniques like MRI or when using x-ray radiation.

In the embodiment illustrated in FIG. 1, the distal end of the catheter 12 has been introduced into a chamber of the heart 11 and advanced to a position where tissue 9 is located which is suitable for ablation. This device may also be used in a vein or at any other locations within the body.

As indicated, the gas expansion chamber preferably takes the form of a hemispheric configuration made of a metallic material, but may be fabricated from numerous other metallic or polymeric materials so long as these materials exhibit the characteristics of being able to withstand a reasonably high internal pressure and are able to withstand the very low temperatures required in the cryoablation process.

The catheter device according to the invention is generally intended to be used to ablate surface tissue inside the heart, or in blood vessels adjacent to the heart, such as the pulmonary vein, but may be used to ablate tissue at any location within the body.

It should be noted that only one embodiment of the present invention has been illustrated. Other embodiments are possible as well. The heat exchanger 25 for instance may be integrated into the handle 15. Alternatively, the cooling chamber may take the form of a distendable material and may be formed from any flexible, fluid-impervious material.

Figure 2:
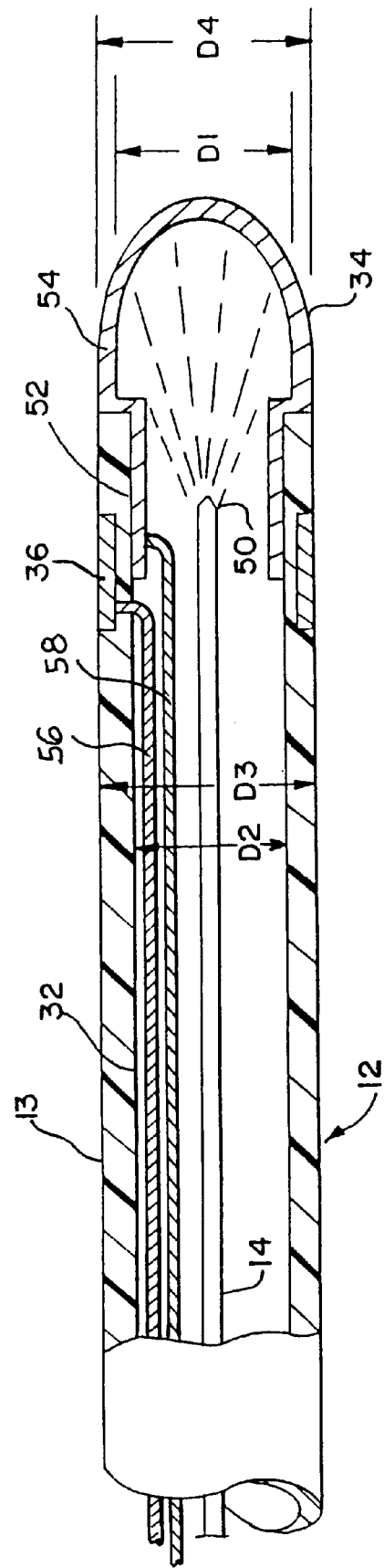

FIG. 2 generally illustrates in detail an embodiment of the distal section of the catheter 12 which includes an outer body 13 having a lumen 32 extending therethrough. The distal tip of the outer body 13 is sealed off by a hemispherical chamber, or cooling dome 34. The cooling dome 34 is formed of a material which exhibits the characteristics of being both conductive to heat and to electrical signals. A ring electrode 36 is disposed around the outer circumference of the outer body 13 at a position slightly proximal of the cooling dome 34. The tubular inner body 14 which is disposed coaxially within the lumen 32 of the outer body 13 provides a conduit for carrying a cooling fluid to a location proximal of the cooling dome 34. The inner body 14 is provided with a nozzle 50, which preferably takes the form of a Jewel-Thompson fluid expansion nozzle, for expanding the fluid in the cooling dome 34 thereby causing cooling to occur within the cooling dome 34.

In this operation, once fluid is expanded by the nozzle 50 to cool the dome 34, the fluid is returned back through the lumen 32 of the outer body 13 to the proximal end of the catheter 12 for removal from the system.

It is an object of the present invention to provide a cryoablation chamber which provides very efficient cooling thereby significantly increasing the operating efficiency of the cryoablation catheter. As illustrated in FIG. 2, this efficiency is accomplished by significantly increasing the interior volume of the cooling space within the cooling dome 34 and also by significantly reducing the wall thickness of the dome 34.

More particularly, the dome 34 includes a reduced diameter neck portion 52 which extends into the lumen 32 of the outer body 13 for retaining the dome 34 at the distal end of the catheter. In addition, the dome 34 is formed in a generally hemispherical configuration and includes a cylindrical side wall 54 which is of a thickness (one-half of D4 minus D1) significantly less than the wall thickness of the outer body 13 (one-half of D3 minus D2).

Preferably, the wall thickness of the dome 34 (one-half of D4 minus D1) is equal to approximately one-half of the thickness of the outer body 13 (one-half of D3 minus D2). In a preferred version of the cryoablation catheter, the wall thickness of the cooling dome 34 is equal to approximately 0.10 millimeters and the wall thickness of the outer body 13 is equal to approximately 0.22 millimeters. In addition, the outside diameter (D4) of the cooling dome 34 is equal to approximately the outside diameter of the outer body 13 (D3).

The ring electrode 36 is disposed on the surface of the outer body 13 at a position proximal of the cooling dome 34. Both the ring electrode 36 and the cooling dome 34 are connected through conductors 56 and 58 respectively to the proximal end of the catheter for connection to control circuitry for heart mapping.

With this design of the cooling dome 34, a large volume of internal space is provided for expansion of the cooling fluid. In addition, the thin wall design of the cooling dome 34, results in cooling which is very quickly transmitted to the outside surface of the dome 34. Accordingly, with this catheter concept there is almost immediate cooling of the outside surface of the dome while at the same time providing a very efficient fluid expansion chamber.

It should be noted that only one embodiment of the present invention has been illustrated, however, other embodiments are possible as well. For example, the cooling dome can take various configurations and may be formed of various metallic or non-metallic materials. The ratio of the thickness of the conductive dome to the thickness of the outer body of the catheter may be varied over a rather large range, however, preferably the wall thickness of the conductive dome is as thin as possible consistent with the internal pressure applied to this surface. These and other modifications will become apparent to those having ordinary skill in the art to which this invention relates and are intended to be within the scope of the claims which follow.

These and other modifications would be apparent to those having ordinary skill in the art to which this invention relates and are intended to be within the scope of the claims which follow.

That which is claimed is:

1. A cryoablation catheter comprising:

an elongated flexible outer tubular member having a lumen extending throughout the length of the tubular member and having a proximal and distal end and an inside and outside diameter;

an inner tubular member extending throughout the length of the outer tubular member and having a proximal end adapted to be coupled to a source of cryoablation fluid;

a generally cylindrical fluid expansion cooling chamber bonded to the distal end of the outer tubular member and being in fluid engagement with the lumen of the outer tubular member, and having an inside diameter substantially greater than the inside diameter of the outer tubular member and an outside diameter substantially equal to the outside diameter of the outer tubular member; and, a fluid expansion nozzle disposed on the distal end of the inner tubular member and extending into the cooling chamber so that when a cooling fluid is supplied to the proximal end of the inner tubular member the fluid is caused to expand at the nozzle to thereby cause cooling to occur within the cooling chamber.

2. A cryoablation catheter as defined in claim 1, wherein said fluid expansion cooling chamber generally takes the form of a hemisphere having an inside wall diameter substantially greater than the inside diameter of the outer tubular member and an outside wall diameter substantially equal to the outside diameter of the outer tubular member.

3. A cryoablation catheter as defined in claim 2, wherein said outer tubular member has a predetermined wall thickness and said expansion cooling chamber has a wall thickness which is equal to approximately one-half of the predetermined wall thickness of the outer tubular member.

4. A cryoablation catheter as defined in claim 2, wherein said expansion cooling chamber includes walls which are formed of a material which permits the transfer of heat through such walls.

5. A cryoablation catheter as defined in claim 2, wherein said expansion cooling chamber includes side walls having a thickness of approximately 0.10 of a millimeter.

6. A cryoablation catheter as defined in claim 2, wherein said fluid expansion nozzle takes the form of a Joule-Thompson fluid expansion nozzle.

7. A cryoablation catheter as defined in claim 6, wherein the proximal end of said inner tubular member is coupled to a source of cooling gas.

8. A cryoablation catheter as defined in claim 7, wherein said cooling gas is nitrous oxide.

9. A cryoablation catheter as defined in claim 2, wherein the fluid expansion chamber is formed of an electrically conductive material and an electrical conductor connected to the fluid expansion chamber and extending to the proximal end of the catheter in order to provide a distal electrode for heart mapping.

10. A cryoablation catheter as defined in claim 9, which includes an intermediate ring electrode mounted on the outer tubular member at a position proximal to the fluid expansion chamber and having an electrical conductor connected to the ring electrode and extending to the proximal end of the catheter.

* * * * *